US005686287A

United States Patent [19]
Baxendale

[11] Patent Number: 5,686,287
[45] Date of Patent: Nov. 11, 1997

[54] MAREK'S DISEASE VIRUS VACCINE

[75] Inventor: William Baxendale, Huntingdon, United Kingdom

[73] Assignee: Akzo Nobel N.V., Arnhem, Netherlands

[21] Appl. No.: 502,078

[22] Filed: Jun. 14, 1995

[30] Foreign Application Priority Data

Jul. 14, 1994 [EP] European Pat. Off. ............ 94202047

[51] Int. Cl.$^6$ .............................. C12N 7/00; C12N 7/02; C12N 7/04; C12N 7/08
[52] U.S. Cl. .................. 435/235.1; 435/239; 435/236; 435/237; 424/229.1; 530/350; 530/826
[58] Field of Search ................. 424/229.1; 435/239; 530/350, 826

[56] References Cited

U.S. PATENT DOCUMENTS

| | | | |
|---|---|---|---|
| 4,673,572 | 6/1987 | DeBoer | 424/89 |
| 4,895,717 | 1/1990 | Witter . | |
| 4,895,718 | 1/1990 | Witter . | |
| 5,283,191 | 2/1994 | Morgan et al. | 435/252.3 |
| 5,378,467 | 1/1995 | Bexendale | 424/202.1 |

FOREIGN PATENT DOCUMENTS

| | | |
|---|---|---|
| 0 159 743 | 10/1985 | European Pat. Off. . |
| 0 496 135 | 7/1992 | European Pat. Off. . |
| WO 85/04588 | 10/1985 | WIPO . |
| WO 93/00112 | 1/1993 | WIPO . |

OTHER PUBLICATIONS

Webster's Ninth New Collegiate Dictionary, p. 984, 1990.

*Primary Examiner*—Lynette F. Smith
*Assistant Examiner*—Brett L. Nelson
*Attorney, Agent, or Firm*—Mary E. Gormley; William M. Blackstone

[57] ABSTRACT

The present invention is concerned with a new strain of Mareks Disease Virus and to a vaccine for the protection of poultry against Mareks Disease containing the novel strain. The invention also relates to bivalent or polyvalent vaccines comprising in addition other viruses of the Mareks Disease virus group, i.e. HVT.

18 Claims, 2 Drawing Sheets

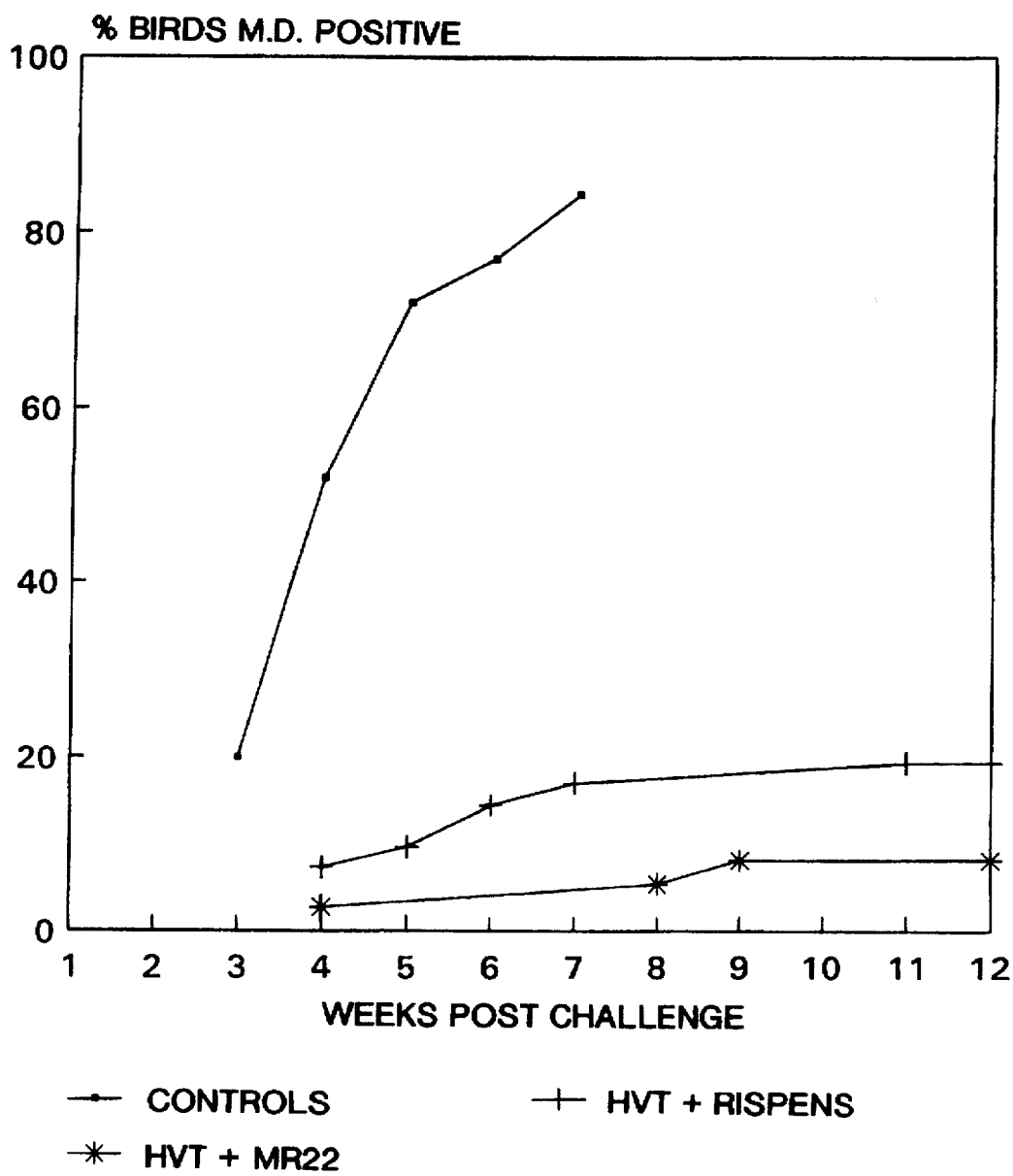
FIG 2 EFFICACY STUDY COMPARING THV + RISPENS OR THV + MR22 IN BIRDS WITH Mab
(SEE EXAMPLE 3)
Mab = MATERNAL ANTIBODY

5,686,287

MAREK'S DISEASE VIRUS VACCINE

FIELD OF THE INVENTION

The present invention relates to a new strain of Marek's Disease Virus (MDV), and to a vaccine for the protection of poultry against Marek's Disease (MD) containing this novel strain. The invention is also concerned with a process for the preparation of such a vaccine.

BACKGROUND OF THE INVENTION

Marek's Disease is a malignant, lympho-proliferative disease of domestic fowl, caused by an infection with a herpesvirus: Marek's Disease Virus. MD is ubiquitous, occurring in poultry-producing countries throughout the world. The causative virus is highly contagious and readily spreads to susceptible birds. Chickens raised under intensive production systems will inevitably suffer losses from MD.

MD affects chickens from about 6 weeks of age, occurring most frequently between the ages of 12 and 24 weeks.

Three forms of MD are recognized clinically, classical MD, acute MD and transient paralysis.

Classical MD is characterized by peripheral nerve enlargement caused by lymphoid infiltration and demyelination, and paralysis is the dominant clinical sign. Mortality is variable, but normally under 10 to 15%.

In the acute form there are multiple and diffuse lymphomatous tumours in the visceral organs. Mortality from this form of MD is usually higher than from the classical form. An incidence of 10 to 30% is common in unvaccinated flocks and outbreaks involving up to 70% of the flock may occur. The pathological lesions in both classical and acute MD are essentially the same, involving the proliferation and infiltration of malignantly transformed T-lymphoblasts into normal tissues, peripheral nerves in the case of the classical form, and visceral organs in the case of the acute form.

Furthermore, MDV has been shown to be responsible for encephalitis in young chickens, which is characterized by sudden paralysis.

There are three distinct serotypes of MD related viruses found in chickens:

Type I : the pathogenic and oncogenic form responsible for the disease in chickens, including high and low virulence forms and attenuated non-pathogenic strains derived therefrom;

Type II non-pathogenic and non-oncogenic strains of MDV;

Type III: herpesvirus of turkeys (HVT), which is non-pathogenic to chickens.

Several practical Marek's Disease vaccines have been developed and are currently in use today. One of the earliest MD vaccines consisted of the serotype III virus, which was originally isolated from turkeys, (see Witter et al. Am. J. Vet. Res., 31, 525–538, (1970)). HVT is used extensively as a vaccine against MD. It is commonly used as a cell-associated preparation, however, substantial amounts of cell-free virus can be extracted from infected cells and a cell-free vaccine has been described in U.S. Pat. No. 3,647,861.

Serotype II MD viruses are naturally occurring non-oncogenic viruses, which thus do not have the potential for causing tumours in vaccinated chickens. These viruses do not, in consequence, require any artificial attenuation by serial passaging and, since they are in their natural state, cannot revert to a virulent form. The SB-1 strain (U.S. Pat. No. 4,160,024) was originally administered as a cell-associated preparation. Such a vaccine, in practice, has to be stored and transported in liquid nitrogen at about −196° C. This serotype II strain has been found to be poorly protective on its own and is, therefore, usually administered in combination with HVT as a bivalent vaccine, since the two viruses together produce greater protection than does either one alone. This phenomenon is called "protective synergy".

European patent application No. 90 314297 describes a vaccine comprising a cell-free form of SB-1. Even in the cell-free form the SB-1 strain is still not very protective on its own and is, in consequence, administered with HVT.

Several vaccines comprising attenuated serotype I MDV have been developed and are in use today.

WO 85/04588, for example, describes an attenuated strain derived from the parent virus MDV CV1-988. All the vaccine preparations described in this publication contained the virus in cell-associated form.

U.S. patent application Ser. No. 7,723,037 describes an attenuated revertant serotype I MD vaccine. The strain used in this vaccine does not produce cell-free virus.

Thus, to date all serotype I vaccines have had to be administered as cell-associated preparations, with the attendant disadvantages of having to be stored and transported in liquid nitrogen. When a vaccine is not stored or handled correctly there is a decrease in the viability of the virus with consequential failure of the vaccination. In countries where liquid nitrogen storage is not practical or available, it is impossible to employ cell-associated MD vaccine.

Furthermore, the MDV containing particles suspended in a cell-associated preparation are liable to vaccine precipitate, and therefore the suspension requires homogenization before administration. Inadequate homogenization may result in an incorrect dose of vaccine and consequently lead to failure of the vaccination. Moreover, the strictly cell-associated nature of said vaccines is responsible for the susceptibility of the vaccines to physical abuse. Damage to the infected cells by sub-optimal harvesting and freezing procedures, as well as incorrect thawing of the ampoules and handling of the vaccine at the hatcheries, will cause cell damage and death and subsequent loss of vaccine titres.

Maternal derived antibodies (MDA) to all MD viral serotypes are ubiquitous in commercial chicks, due to natural exposure of breeders to MD viruses and/or vaccination of breeders with serotypes I, II and III viruses. Such MDA are passed to the offspring and reduce the efficacy of any subsequent vaccination.

Whilst it is impossible to control MDA to serotypes I and II MDV, it is possible to control MDA to serotype III MDV, i.e. HVT, by vaccinating breeder flocks with MDV vaccines lacking HVT, so that their progeny may be better protected when vaccinated with HVT-containing monovalent, bivalent or polyvalent vaccines. Such a vaccination strategy is called "alternate generation" vaccination. In countries where liquid nitrigen storage and transporting facilities are not available it is not possible to practice this alternate generation vaccination, since the only freeze-dried MDV vaccine available contains HVT. Thus there is a need for a freeze-dried serotype I MDV vaccine.

Earlier work with serotype I MD viruses demonstrated that the amount of cell-free virus, measured as pfu (plaque forming units) was of inadequate titre to be useful for vaccination purposes (U.S. Pat. No. 4,895,718; Witter, R. L. et at., Avian Diseases 31,829, 1987; Powell, P. C., World's Poultry Science Journal 42, 205, 1986; Schat, K. A., Internews 3, 13, 1989).

SUMMARY OF THE INVENTION

However, a new strain of serotype I MDV has been found which, following attenuation by serial passage in chick cell cultures produces large amounts of cell-free virus and is more protective than any serotype I MDV used to date. As a result it is possible to produce a freeze-dried serotype I MDV vaccine. Even when cell-associated this strain has been found to be more protective than the best MDV serotype I vaccine currently available.

BRIEF DESCRIPTION OF THE DRAWINGS

FIG. 2 is a graph showing the comparison of the immunity induced by the MR22+HVT vaccine and the Rispens+HVT vaccine, as described in Example 3.

DETAILED DESCRIPTION OF THE INVENTION

Figure 1:
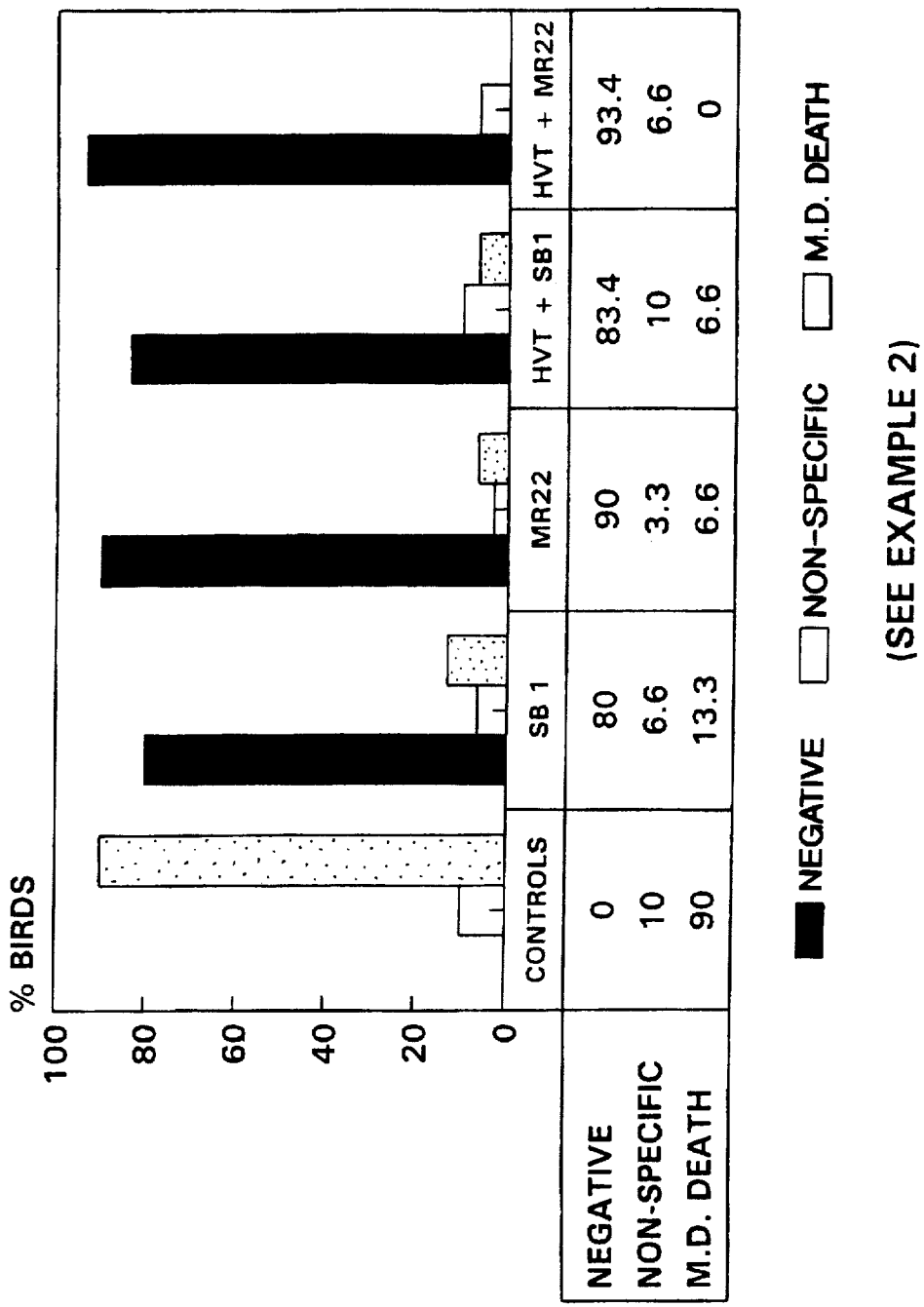
FIG. 1 is a bar graph showing the comparison of efficacy of cell-free Marek's Disease vaccines with challenge by strain RB1B, as described in Example 2.

According to one aspect of the invention there is provided a novel attenuated strain of Marek's Disease Virus serotype I which, when liberated from infected cells by sonication, results in, at most, a 100-fold decrease in cell-free virus titre compared with the cell-associated virus titre.

Preferably the attenuated strain produces at most a 50-fold decrease in cell-free virus titre, most preferably a 10-fold decrease in cell-free virus titre. Clearly it is desirable that, following sonication, there is no drop in cell-free virus titre, when compared with the cell-associated virus titre.

An attenuated cell-free strain of MDV serotype I in accordance with the present invention was deposited on 24 Jun. 1994 with the European Collection of Animal Cell Cultures, Porton Down, United Kingdom under the Budapest Treaty, and designated accession No. V94062211.

One strain of MDV serotype I, in accordance with the invention and hereinafter referred to as MR22, was isolated on chick embryo kidney cell cultures from buffy coat cells taken from a flock in the field in 1971. It was then passaged 18 times in chick embryo fibroblast (CEF) cell cultures prepared from SPF (specific pathogen free) eggs. This isolate was passaged a further two times in secondary CEF cells, then a cell free preparation was made by sonicating infected cells in the presence of S.P.G.A. stabilizer (Bovarnik et al., J. Bact., 59, 509. 1950.).

The MR22 strain obtained as described above was shown to be an MDV serotype I virus by the fact that it reacted with monoclonal antibodies 2092 and 4859, but failed to react with monoclonal antibodies that react with serotype II and III virus. These antibodies were prepared and used as described by Lee, L. F., J. Immunology, 130, 1003–1006, (1983), and Silva and Lee, Virology, 136, 307–320, (1984). Table 1 shows the results of fluorescent antibody studies using different MDV strains/serotypes against specific monoclonal antibodies.

TABLE 1

The reaction pattern of M.D. strains with four monoclonal antibodies (fluorescent antibody results).

| Virus | Sero-type | Mono-clonal H19 | Monoclonal 2BN | Monoclonal Y5.9 | Monoclonal L78.2 |
|---|---|---|---|---|---|
| HPRS 16 | 1 | ++ | ++ | − | − |
| VICTORIA | 1 | + | + | − | − |
| RISMAVAC | 1 | − | + | − | − |
| CLONE C | 1 | − | + | − | − |

TABLE 1-continued

The reaction pattern of M.D. strains with four monoclonal antibodies (fluorescent antibody results).

| Virus | Sero-type | Mono-clonal H19 | Monoclonal 2BN | Monoclonal Y5.9 | Monoclonal L78.2 |
|---|---|---|---|---|---|
| MR22 | 1 | + | + | − | − |
| LPSB1 | 2 | − | − | ++ | − |
| HP SB1 | 2 | − | − | ++ | (+/−) |
| HVT/PB1 | 3 | − | − | − | ++ |

Table 2 shows that the amount of cell free MR22 virus obtained when infected chick embryo fibroblasts are sonicated in the presence of the stabilizer SPGA is considerably greater than other serotype I strains available.

TABLE 2

| Strain | Serotype | Cell associated titre (pfu/ml) | Cell free titre (pfu/ml) | Difference |
|---|---|---|---|---|
| HPRS-16 | 1 | $10^6$ | $<10^2$ | >10,000:1 |
| Rispens (CVI988) | 1 | $10^6$ | $10^2$ | 10,000:1 |
| MR22 | 1 | $10^{5.7}$ | $10^{4.7}$ | 10:1 |

The MR22 strain was further passaged through a chicken, virus was isolated subsequently and passaged twice in CEF after which the virus was passaged in a chicken as a cell-free virus. After re-isolation the virus was passaged a further six times in CEF (=MSV, master seed virus). The potency of the virus to release high amounts of cell-free virus was tested several times in separate experiments.

TABLE 3

| | Titre of virus yield (pfu/ml) | | |
|---|---|---|---|
| Passage level | Cell associated | Cell free | Difference |
| MSV + 2 | $10^{6.3}$ | $10^{4.8}$ | 32:1 |
| MSV + 6 | $10^{6.9}$ | $10^{5.4}$ | 32:1 |
| MSV + 6 | $10^{6.8}$ | $10^{6.1}$ | 5:1 |
| MSV + 6 | $10^{5.6}$ | $10^{4.7}$ | 8:1 |

A further MDV serotype 1 strain which produces a large amount of cell free virus is Victoria 10, a strain isolated from a healthy flock in the UK in the mid-eighties. The virus was passaged 10 times in chicken kidney cells (CK) and 18 times in CEFs. The development of cell free virus yield is given below:

TABLE 4

| | Titre of virus yield (pfu/ml) | | |
|---|---|---|---|
| Passage level | Cell associated | Cell free | Difference |
| CK10CEF6 | $10^{5.9}$ | $10^{3.4}$ | 316:1 |
| CK10CEF11 | $10^{6.2}$ | $10^{5.2}$ | 10:1 |
| CK10CEF18 | $10^{5.6}$ | $10^{4.6}$ | 10:1 |

The advantage of this greater production of cell-free virus by MR22, Victoria 10 or any other MDV serotype 1 strain is that it is possible to prepare a freeze-dried vaccine preparation, which in turn removes the need for storing and transporting the vaccine in liquid nitrogen. To date, no freeze-dried serotype I MDV vaccine has successfully been produced.

To propagate the MR22 strain for vaccine production roller cultures seeded with CEF cells can be inoculated with cell-associated or cell-free virus obtained as described above. After an incubation period of several days the supernatant medium is discarded and the cells removed with a trypsin-versene mixture, after which the cells are deposited by centrifugation and the supernatent is discarded.

In order to prepare the cell-free virus the deposited cells are suspended in buffer, for example in phosphate-buffered saline (PBS) or preferably in a medium containing a stabilizer, SPGA being the most preferred.

Cell disruption may be effected by several methods, e.g. sonication or freeze-thaw. The presence of any intact cells can be determined by examination in a hemocytometer. The sonicated or quick frozen preparation can be filled into vials and can then be freeze-dried, if desired in the presence of EDTA. Optionally, before freeze-drying, the cellular debris is removed by filtration or centrifugation.

Cell-free serotype I MDV obtained by the method described above can be incorporated into vaccines as live or inactivated virus.

The vaccine containing live virus can be prepared and marketed in the form of a suspension, or it can be lyophilized.

Lyophilized vaccines preferably contain one or more stabilizers. Suitable stabilizers include, for example, SPGA, carbohydrates such as sorbitol, mannitol, starch, dextran or glucose, proteins such as albumin or casein, or degradation products thereof, and buffers such as alkali metal phosphates. If desired, one or more compounds with adjuvant activity can also be added. Suitable compounds for this purpose include vitamin E acetate o/w-emulsion, aluminium hydroxide, phosphate or oxide, mineral oil (such as Bayol F and Marcol 52 (registered trade marks)) and saponins.

As a matter of course, the MDV serotype 1 strains specifically mentioned herein, in particular strain MR22 can be used as the active component in a MDV vaccine in a cell associated form. Such vaccines, live or inactivated, can be prepared according to conventional methods.

The aim of inactivation of the MD viruses is to eliminate reproduction of the viruses. In general, this can be achieved by chemical or physical means. Chemical inactivation can be effected by treating the viruses with, for example, enzymes, formaldehyde, β-propiolactone, ethylene-imine or a derivative thereof, an organic solvent (such as Tween, Triton [Registered Trade Marks], sodium desoxy-cholate, sulphobetain or cetyl trimethylammonium salts). If necessary, the inactivating substance is neutralized afterwards; material inactivated with formaldehyde can, for example, be neutralized with thiosulphate. Physical inactivation can preferably be carried out by subjecting the viruses to energy-rich radiation, such as UV light, X-radiation or γ-radiation. If desired, the pH can be brought back to a value of about 7 after treatment.

Usually, an adjuvant, selected from the list mentioned above, and, if desired, one or more emulsifiers, such as Tween and Span (Registered Trade Marks), are also added to the inactivated virus material.

The vaccine is administered in an effective dosage of the viral agent, i.e. the amount of immunizing cell-free virus material that will induce immunity in a chicken against challenge by a virulent MD virus. Immunity is defined as the induction of a significantly higher level of protection in a population of chickens after vaccination, compared to an unvaccinated group.

For live vaccines the dose rate per chick may range from 1 to 6 $logs_{10}$ pfu.

Typically, the live vaccine according to the invention is administered in a dose of at least 2.2 $logs_{10}$ pfu cell-free virus, preferably in a dose of at least 2.7 $logs_{10}$ pfu cell-free virus, more preferably in a dose of at least 3.2 $logs_{10}$ pfu.

In the case of a natural route of administration, e.g. spray, eye and nose drops, a dose of $10^6-10^7$ pfu/chick may be administered.

Inactivated vaccines may contain the antigenic equivalent of 3 to 7 $logs_{10}$ pfu per bird dose, preferably between 4 to 6 $logs_{10}$ pfu.

Vaccines according to the invention may be administered by spray at high titre, eye drop, nose drop, orally (e.g. in the drinking water), or by means of intramuscular, subcutaneous or in ovo injection at any age after the chicken obtains immunocompetence. Normally the vaccine is administered to the chick 24–48 hours after hatching.

Another aspect of this invention is the combination of cell-free MDV serotype I with cell-free HVT as a bivalent vaccine. Surprisingly, it has been found that the cell-free MDV serotype I is still able to augment the efficacy of HVT, despite the increased stage of passaging.

In particular, cell-free serotype I MDV of the MR22 strain are used in combination with cell-free HVT. The HVT virus to be incorporated into a vaccine according to the invention may be of any available strain, e.g. FC126 or THV PB1 (commercially available from Intervet Inc.). Optionally, the HVT virus comprises a foreign gene encoding an antigen of another poultry pathogen, inserted into its viral genome, forming a polyvalent vaccine.

Still another aspect of this invention is the combination of cell-free MDV serotype I with cell-free MDV serotype II as a bivalent vaccine, or with both cell-free MDV serotype II and cell-free HVT as a trivalent vaccine. Preferably the SB-1 strain or the HPRS B-24 strain are used as MDV serotype II strain. The MDV serotype II strain can also be genetically manipulated to incorporate an antigen of another poultry pathogen.

The invention also includes combination vaccines comprising, in addition to the cell-free serotype I MD viral material, a vaccine derived from other pathogens infectious to poultry. The cell-free serotype I MDV can be administered in combination with a vaccine virus selected from the group consisting of Newcastle Disease virus (NDV), Infectious Bronchitis virus (IBV) and Infectious Bursal Disease virus (IBDV).

EXAMPLE 1

A. Passaging of Serotype 1 MD Virus MR22.

Following the initial isolation of MR22 on chick embryo kidney cell cultures it was passaged on chick embryo fibroblast (CEF) cell cultures.

Cell associated MR22 virus is inoculated onto 24 hour old SPF derived CEF cell cultures grown on 6 cm diameter Falcon Petridishes (1.5×10 CEF/dish).

0.1 ml of inoculum containing at least 100 pfu in inoculated into the 5 ml of tissue culture medium on the plates and the cell associated virus settles on the monolayer and infects them.

After an incubation period of 5 days at 38.5° C. in a CO atmosphere of 5%, the cells are removed from the dishes by:

1. Pouring off the medium.
2. Adding trypsin versene PBS solution to loosen the attachment of the cells to the petri dish.
3. Discarding the trypsin/versene PBS mixture before the cells detach from the petri dish.

4. Washing the cells off the dishes with growth medium.

The suspension of cell associated virus obtained from step 4 is used as inoculum for the next passage on CEF cells. The viruses were passaged 18 times as described above.

B. Preparation of MR22 cell-free serutype 1 MD vaccine

Two roller cultures (1750 cm) seeded with 200×10 CEF cells were inoculated into the medium with 1 ml of cell-associated MR22 seed virus, obtained by the method described above, with a titre of approximately 10 pfu/ml after 24 hours incubation.

After a further incubation period of 5 days the supernatant medium was discarded and the cells removed with a trypsin versene mixture. The cells were deposited by centrifugation, the supernatent discarded and the cells mixed with 20 mls of SPGA stabilizer and then ultrasonicated for 20 secs.

The sonicated preparation was filled out in 1 ml aliquots in vials and freeze dried.

| Titre pre freeze drying  | $10^{4.7}$ pfu/ml  |
|---|---|
| Titre post freeze drying | $10^{4.5}$ pfu/ml. |

EXAMPLE 2

Comparative Efficacy of Cell-Free Mareks Disease Vaccines

Day-old SPF chicks were divided into groups of 30, placed in negative pressure isolators and each group was vaccinated intramuscularly with 0.1 ml/chick of one of the following vaccines or combination of vaccines:

A) SB1 (cell-free type II vaccine strain MR30, Intervet, Boxmeer, the Netherlands) at a dose of 200 pfu/chick.

B) MR22 (cell-free type I vaccine) at a dose of 200 pfu/chick.

C) HVT (cell-free type III vaccine strain PB-1, Intervet) at a dose of 1000 pfu/chick and SB1 (cell-free type II vaccine, strain MR30, Intervet) 200 pfu/chick.

D) HVT (cell-free type III vaccine strain PB-1, Intervet) at a dose of 1000 pfu/chick and MR22 200 pfu/chick.

At 7 days post vaccination all groups together with another group of 30 SPF chicks were challenged with virulent RB1B Mareks Disease virus at a dose rate of 250 pfu/chick, 0.1 ml/chick given intramuscularly.

The chicks were observed until the end of the experiment at 91 days. Any chick that died was autopsied and the cause of death established. At the end of the experiment all remaining birds were killed and autopsied.

The number of chicks dying of MD by the end of the experiment indicated that the challenge was severe (see FIG. 1). All control chicks had died by 56 days; 90% due to Mareks disease and 10% due to nonspecific causes. The birds remaining alive in the group receiving SB 1 vaccine alone were all killed at 63 days because they had started to show an unacceptable level of MD, 13.3% having died from MD already by that time.

This experiment demonstrated that MR22 in a cell-free state given alone, or in combination with HVT, protected well against a severe Mareks Disease challenge.

EXAMPLE 3

Comparison of the Immunity Induced by MR22+HVT Vaccine Compared With Rispens+HVT The virus strains used were as follows:

1. HVT cell-associated vaccine (strain FC 126-Intervet).

2. Rispens cell-associated vaccine (strain CVI988-Intervet).

3. MR22 cell-associated vaccine.

Groups of approximately 40 one-day-old chicks were placed in negative pressure isolators and vaccinated with one of the following combinations of cell-associated vaccines. The chicks were shown to have maternally derived antibodies to serotype I, II and III (MDA-positive).

Group A

These chicks received 1000 pfu of HVT and 1000 pfu of Rispens given in 0.1 ml intramuscularly.

Group B

These chicks received 1000 pfu of HVT and 1000 pfu of MR22 vaccine both given in 0.1 ml intramuscularly.

At 5 days of age groups A and B were challenged together with a control group of 40 5-day-old unvaccinated chicks. All chicks received 500 pfu of the virulent Mareks virus RB1B in the cell-associated form intramuscularly. All birds were observed for 12 weeks. Any birds showing signs of MD were killed and these, together with any bird that died, were autopsied to establish the cause of death. Where necessary histological examination of tissue was performed. At the end of the experiment all birds were killed and autopsied to establish the presence of MD lesions.

The incidence of MD in the control unvaccinated chicks was very high (see Table 5 and FIG. 2). A high level of immunity was evident in both vaccinated groups with Group B showing the better protection against this virulent challenge.

TABLE 5

Incidence of M.D. following challenge with RB1B of control and vaccinated birds.

| | Number of birds at start | Non specific deaths | M.D. tumors | M.D. by histology | Total M.D. | % M.D. |
|---|---|---|---|---|---|---|
| Controls     | 39 | 0 | 34 | 3 | 37 | 94 |
| HVT + Rispens | 41 | 0 | 9  | 4 | 13 | 31 |
| HVT + MR22   | 38 | 1 | 3  | 2 | 5  | 13 |

These results demonstrate that, in the cell-associated form, MR22+HVT protect better against a severe challenge of RB1B MDV than Rispens+HVT, which is currently the best vaccine available commercially.

I claim:

1. An attenuated strain of Marek's Disease Virus serotype I which, when liberated from infected cells by sonication, results in at most a 100-fold decrease in cell-free virus titre compared with the cell-associated virus titre.

2. An attenuated strain according to claim 1 which results in at most a 50-fold decrease in cell-free virus titre.

3. An attenuated strain according to claim 1 which results in at most a 10-fold decrease in cell-free virus titre.

4. An attenuated strain according to claim 1 in cell-associated form.

5. An attenuated strain according to claim 4, which is the strain of Marek's Disease Virus serotype I deposited at the European Collection of Animal Cell Cultures, Porton Down, UK under accession No. V94062211.

6. An attenuated strain according to claim 1 in cell-free form.

7. An attenuated cell-free strain of Marek's Disease Virus serotype I which is deposited at the European Collection of Animal Cell Cultures, Porton Down, UK under accession No. V94062211.

8. A vaccine for use in the protection of poultry against Marek's Disease comprising the attenuated Marek's Disease Virus serotype I according to claim 1 and a pharmaceutically acceptable carrier.

9. A vaccine according to claim 8, further comprising cell-free HVT.

10. A vaccine according to claim 8, further comprising cell-free MDV serotype II.

11. A vaccine according to claim 8, further comprising antigens derived from other poultry pathogens.

12. A vaccine according to claim 8, wherein the vaccine is lyophilized.

13. A method for the preparation of a vaccine that protects poultry against Marek's Disease which comprises:
  (a) growing a serotype I Marek's Disease virus in cell culture from which sufficient quantities of cell-free virus necessary to prepare an effective immunizing dosage can be obtained,
  (b) disrupting the cells,
  (c) subsequently collecting the cell-free viruses, and
  (d) subjecting the material obtained from step (c) to at least one of the following treatments:
    i clarifying by centrifugation and/or filtration;
    ii adding buffer;
    iii adding a stabilizing agent;
    iv putting the material in a vial;
    v freeze-drying.

14. A method of controlling Marek's Disease in poultry comprising administering to the poultry the vaccine according to claim 8.

15. A vaccine according to claim 9, further comprising cell-free MDV serotype II.

16. A vaccine according to claim 9, further comprising antigens derived from other poultry pathogens.

17. A vaccine according to claim 10, further comprising antigens derived from other poultry pathogens.

18. A vaccine according to claim 15, further comprising antigens derived from other poultry pathogens.

* * * * *

UNITED STATES PATENT AND TRADEMARK OFFICE
CERTIFICATE OF CORRECTION

PATENT NO. : 5,686,287
DATED : November 11, 1997
INVENTOR(S) : William Baxendale It is certified that error appears in the above-indentified patent and that said Letters Patent is hereby corrected as shown below:

correct the filing date on the title page by deleting "Jun. 14, 1995" and inserting -- July 14, 1995 --.

Signed and Sealed this

Twenty-fourth Day of February, 1998

Attest:

BRUCE LEHMAN

Attesting Officer       *Commissioner of Patents and Trademarks*